United States Patent
Ranjan et al.

(10) Patent No.: US 7,345,201 B2
(45) Date of Patent: Mar. 18, 2008

(54) PROCESSES FOR PREPARING SERTRALINE

(75) Inventors: Harish Ranjan, New Delhi (IN); Sanjay Nayal, Haryana (IN); Pankaj Singh, Old Faridabad (IN); Vinod Kumar Kansal, Haryana (IN); Marioara Mendelovici, Rechovot (IL)

(73) Assignee: Teva Pharmaceutical Industries, Ltd., Petah Tiqva (IL)

( * ) Notice: Subject to any disclaimer, the term of this patent is extended or adjusted under 35 U.S.C. 154(b) by 0 days.

(21) Appl. No.: 11/361,456

(22) Filed: Feb. 23, 2006

(65) Prior Publication Data

US 2007/0010694 A1    Jan. 11, 2007

Related U.S. Application Data

(60) Provisional application No. 60/656,134, filed on Feb. 23, 2005, provisional application No. 60/704,730, filed on Aug. 1, 2005, provisional application No. 60/763,530, filed on Jan. 30, 2006, provisional application No. 60/763,531, filed on Jan. 30, 2006, provisional application No. 60/773,394, filed on Feb. 14, 2006, provisional application No. 60/773,567, filed on Feb. 14, 2006.

(30) Foreign Application Priority Data

Jan. 25, 2006  (IN)  ............ 220/DEL/2006
Jan. 25, 2006  (IN)  ............ 221/DEL/2006

(51) Int. Cl.
    *C07C 211/00*    (2006.01)
(52) U.S. Cl. ..................... 564/308
(58) Field of Classification Search ............. None
    See application file for complete search history.

(56) References Cited

U.S. PATENT DOCUMENTS

| | | | |
|---|---|---|---|
| 4,536,518 | A | 8/1985 | Welch, Jr. et al. |
| 5,248,699 | A | 9/1993 | Sysko et al. |
| 6,452,054 | B2 | 9/2002 | Aronhime et al. |
| 6,495,721 | B1 | 12/2002 | Schwartz et al. |
| 6,500,987 | B1 | 12/2002 | Schwartz et al. |
| 6,506,940 | B1 | 1/2003 | Jadav et al. |
| 6,593,496 | B1 | 7/2003 | Quallich |
| 6,683,220 | B2 | 1/2004 | Berger et al. |
| 6,809,221 | B2 | 10/2004 | Mendelovici et al. |
| 2002/0019570 | A1 | 12/2002 | Mendelovici et al. |
| 2005/0085669 | A1 | 4/2005 | Hershkovitz et al. |

FOREIGN PATENT DOCUMENTS

| | | |
|---|---|---|
| WO | WO 98/27050 | 6/1998 |
| WO | WO 99/57093 | 11/1999 |
| WO | WO 01/16089 | 3/2001 |
| WO | WO 01/30742 | 5/2001 |
| WO | WO 01/49638 | 7/2001 |

*Primary Examiner*—Samuel A. Barts
(74) *Attorney, Agent, or Firm*—Kenyon & Kenyon LLP

(57) ABSTRACT

Provided are processes for the preparation of sertraline and sertraline hydrochloride.

23 Claims, No Drawings

PROCESSES FOR PREPARING SERTRALINE

RELATED APPLICATIONS

This application claims the benefit of U.S. Provisional Application No. 60/656,134, filed Feb. 23, 2005; U.S. Provisional Application No. 60/704,730, filed Aug. 1, 2005; Indian Application No. 220/DEL/2006, filed Jan. 25, 2006, Indian Application No. 221/DEL/2006 filed Jan. 25, 2006; U.S. Provisional Application No. 60/763,530, filed Jan. 30, 2006; U.S. Provisional Application No. 60/763,531 filed Jan. 30, 2006; U.S. Provisional Application No. 60/773,394, filed Feb. 14, 2006; and, U.S. Provisional Application No. 60/773,567, filed Feb. 14, 2006. The contents of which are incorporated herein by reference.

FIELD OF THE INVENTION

The present invention encompasses processes for preparing sertraline and the hydrochloride salt thereof.

BACKGROUND OF THE INVENTION

Sertraline hydrochloride, (1S-cis)-4-(3,4 dichlorophenyl)-1,2,3,4-tetrahydro-N-methyl-1-naphthalenamine hydrochloride, having the formula:

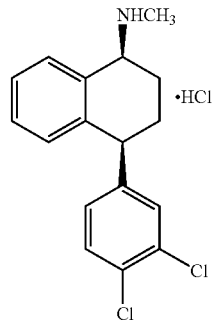

Sertraline hydrochloride is approved under the trademark Zoloft® by the U.S. Food and Drug Administration as a serotonin re-uptake inhibitor for the treatment of depression, obsessive-compulsive disorder, panic disorder and post-traumatic disorder. Only cis sertraline is therapeutically active.

U.S. Pat. No. 4,536,518 ("the '518 patent") describes the synthesis of sertraline hydrochloride from sertralone having the following formula:

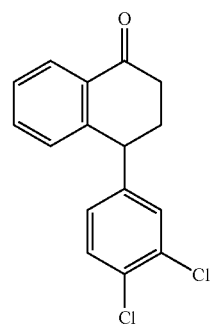

Sertralone

The reported process for synthesizing sertraline from sertralone has two steps. First, sertralone is condensed with methyl amine in the presence of an acid catalyst, to yield the Schiff base of sertralone, 4-(3,4-dichlorophenyl)-3,4-dihydro-1(2H)naphthalenylidene]methanamine ("ketimine"):

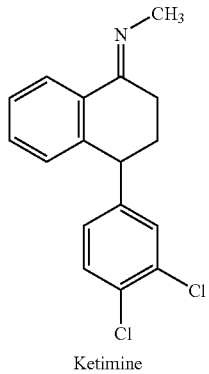

Ketimine

The imine is then reduced to sertraline. The formation of cis/trans sertraline hydrochloride from sertralone is described in the following reaction scheme:

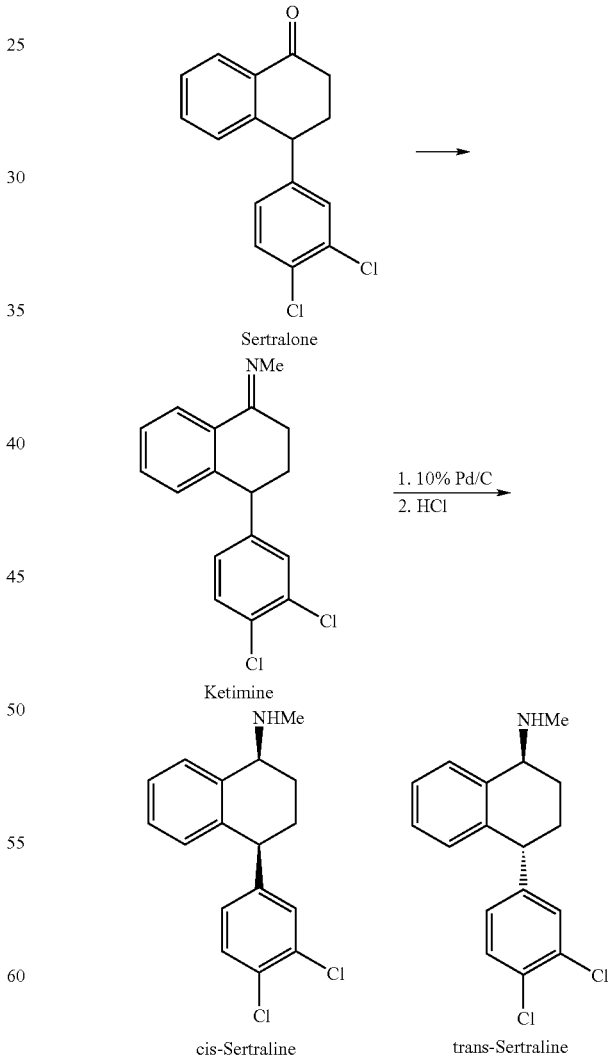

The reduction process disclosed in the '518 patent involves the hydrogenation of ketimine concentrate at room temperature for two hours over 10% Pd/C catalyst in an atmosphere of hydrogen (1 atm pressure). The product is reported to be a racemic mixture of the cis and trans diastereoisomers ("(±)-cis/trans-sertraline") in a ratio of approximately 3 to 1.

International Publication WO 99/57093 reports a process of selective hydrogenation with a palladium catalyst pretreated with an alkali halide. The publication reports that the process of the '518 patent may lead to 10% of dechlorinated side products, while the process of the publication has a "total amount of said contaminated by-products . . . below 0.5%." With regard to the cis/trans ratio, the ratio provided is 85-95% in the description of the invention.

U.S. Pat. No. 6,593,496 reports the preparation of ketimine by reacting sertralone with monomethylamine and either titanium tetrachloride or molecular sieves. The hydrogenation illustrated in scheme 1 is carried out with a palladium catalyst in THF.

US 2003/0105364 reports a process for obtaining optically pure sertralone through chromatography. The examples do not illustrate hydrogenation.

US 2003/0166970 reports a process for making (±)-sertraline with a cis/trans ratio of greater than about 3:1 by hydrogenation of ketimine at a temperature of at least about 40° C. using a palladium or a platinum catalyst.

Two publications, WO 01/30742 and WO 98/27050, report the stereoselective reduction of sertraline imine derivatives. The publication WO 01/30742 reports replacing the methyl group of ketimine with an optionally substituted bulky benzyl group to increase the cis to trans ratio during hydrogenation, followed by the additional steps of converting the bulky group to a methyl group. Additionally, WO 01/30742 reports that "The reduction may be performed using complex hydrides (e.g. $NaBH_4$) or by hydrogenation. Reduction performed by catalytic hydrogenation tends to give better selectivity that reduction using the complex hydrides. For example, aliquots of N-[4-(3,4 dichlorophenyl)-3,4-dihydro-1(2H)-naphthalenylidene]-benzylamine were reduced with $NaBH_4$ and Raney nickel/$H_2$ respectively, and subsequently reductively alkylated with formaldehyde, after which the cis/trans ratio was analyzed. The result was a ratio of 53.8/46.2 using $NaBH_4$ compared to 82.9/17.1 for Raney nickel/$H_2$ which clearly demonstrates the selectivity for the catalytic hydrogenation."

WO 98/27050 reports obtaining sertraline by reducing an N-oxide derivative of the imine. According to Example 1, the N-oxide derivative is hydrogenated with Raney nickel catalyst, while in Example 2 a 10% palladium on carbon is used as a catalyst. A cis product with an 81% yield is reported in both instances. According to WO 98/27050, the N-oxide group may then be removed by addition of HCl to the N-oxide compound in ethanol.

WO 01/16089 discloses a process of reductive amination of sertralone to cis and trans sertraline. According to Example 1, sertralone is reduced in the presence of Raney nickel and methylamine. Example 1 reports a yield of 48-51% of the cis isomer.

Typically, hydrogenation of ketimine over Raney Nickel leads to formation of dechlorinated impurities, where dechlorinated impurities are defined as the total amount of sertraline compounds wherein at least one of the two chlorine atoms of the phenyl group is absent. The level of impurities produced depends on the hydrogen pressure, reaction temperature, and duration of hydrogenation. Therefore, control over the level of impurities on a commercial scale is extremely difficult. Furthermore, removal of these impurities is cumbersome due to the same solubility pattern shared by sertraline and the impurities. Loss of the desired material due to additional purification is also a significant obstacle to the hydrogenation process. There is a need in the art for additional processes for hydrogenation of imines for preparation of sertraline.

SUMMARY OF THE INVENTION

In one embodiment, the present invention provides a process of preparing sertraline comprising the step of reducing ketimine with Raney Nickel under a hydrogen atmosphere, wherein the ketamine is in a mixture with at least one halogenated hydrocarbon and at least one organic solvent.

In another embodiment, the present invention provides a process of removing titanium from ketimine comprising the steps of:
  a) reducing ketimine with Raney Nickel under a hydrogen atmosphere in presence of a titanium containing catalyst, wherein the ketamine is in a mixture with at least one halogenated hydrocarbon and at least one organic solvent;
  b) adding an additional amount of toluene to the reaction mixture;
  c) filtering the mixture to obtain an organic layer;
  d) washing the organic layer;
  e) treating the organic layer with activated carbon followed by filtration;
  f) removing the toluene by distillation to obtain a residue;
  g) combining the residue with cyclohexane; and
  h) recovering the ketamine.

In another embodiment, the present invention provides a process for sertraline HCl comprising the steps of:
  a) reducing sertraline-1-imine in a mixture with toluene and 1,2-dichlorobenzene with Raney Nickel under a hydrogen atmosphere to obtain a racemic mixture;
  b) combining toluene and D(−)mandeleic acid with the mixture to precipitate crude sertraline mandelate;
  c) recrystallizing the crude mandelate from ethanol to obtain a purified mandelate salt;
  d) converting the mandelate salt to the hydrochloride salt.

In another embodiment, the present invention provides sertraline or its hydrochloride salt thereof, having less than about 0.1% of dechlorinated impurities as measured by HPLC or GC.

In another embodiment, the present invention provides pharmaceutical composition comprising sertraline HCl having less than about 0.1% of dechlorinated impurities as measured by HPLC or GC and a pharmaceutically acceptable excipient.

DETAILED DESCRIPTION OF THE INVENTION

The term "dechlorinated impurities" refers to sertraline wherein at least one of the two chlorine atoms of the phenyl group is absent. The following are examples of dechlorinated impurities:

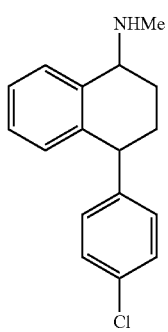

Impurity A

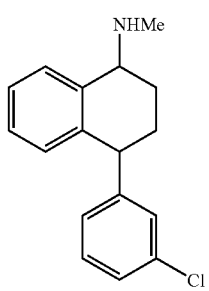

Impurity B

Impurity C

Impurity A refers to the compound where chlorine at the 3-position is absent. Impurity B refers to the compound where chlorine at the 4-position is absent. Impurity C refers to the compound where both chlorine atoms are absent.

The level of impurities in sertraline referred to throughout the application, i.e., "sertraline having less than about 0.1% of dechlorinated impurities," may be measured as area % by HPLC or GC.

In one embodiment, the invention encompasses a process for preparing sertraline by reducing ketimine with Raney Nickel, wherein the ketimine is in a mixture with at least one halogenated hydrocarbon and at least one organic solvent. An advantage of this process is that a product having less than about 0.1% of dechlorinated impurities may be obtained.

Halogenated hydrocarbons may include cyclic or acyclic, saturated or unsaturated aliphatic or aromatic hydrocarbons. Preferred halogenated hydrocarbons include those wherein the hydrocarbon is a $C_1$ to $C_7$ aromatic or aliphatic hydrocarbon. The halogenated hydrocarbon can include any compound wherein one or more hydrogen atoms (preferably from one to three, more preferably one or two) of the $C_1$ to $C_7$ aromatic or aliphatic hydrocarbon is substituted with a halo group selected from fluoro, chloro or bromo, with chloro being particularly preferred.

Halogenated hydrocarbons for use in the present invention includes halogenated aromatic hydrocarbons wherein the hydrocarbon is $C_6$ or $C_7$, e.g. benzene or toluene. The benzene and toluene may be halogenated (preferably with one to three, more preferably one or two halo, preferably chloro, groups) either in the aromatic ring or in the methyl group of toluene.

Also preferred are halogenated hydrocarbons wherein the hydrocarbon is an aliphatic hydrocarbon selected from the group consisting of $C_1$ to $C_4$ alkanes, $C_2$ to $C_4$ alkenes (preferably $C_2$, i.e. ethene) or a $C_4$ diene. Halogenated hydrocarbons for use in the present invention include halogenated aliphatic hydrocarbons wherein the hydrocarbon is a $C_1$ to $C_4$ alkane, alkene or diene, wherein at least one (preferably one to six, more preferably one to three, and most preferably one or two) hydrogen atoms are replaced by fluoro, chloro or bromo, preferably chloro or fluoro, with chloro being most preferred. The most preferred halogenated hydrocarbons are chlorobenzene, o-, m- or p-dichlorobenzene, dichloromethane, and o- or p-chlorotoluene.

The halogenated hydrocarbon may be present in an amount sufficient to reduce or ameliorate dehalogenation Preferably, the halogenated hydrocarbon is present in an amount of about 0.01 mol to about 3.0 mol equivalent of the ketimine, more preferably about 0.5 mol to about 2.0 mol equivalent, and most preferably about 1.0 mol equivalent. The concentration of halogenated hydrocarbons with respect to Ketimine is preferably in the range of about 20% to about 50% weight by volume and most preferably about 50% weight by volume).

Suitable organic solvents are those in which ketimine is soluble. The examples provide many different suitable solvents. Preferably, the organic solvent is a $C_1$-$C_4$ alcohol, $C_3$-$C_6$ ester, $C_6$-$C_{12}$ aromatic hydrocarbon, $C_2$-$C_8$ ether, or $C_3$-$C_7$ amide or mixtures thereof. More preferably, the organic solvent is methanol, ethanol, isopropanol, toluene, tetrahydrofuran, ethyl acetate, dimethylformamide or mixtures thereof. In one embodiment, the organic solvent is a mixture of toluene and methanol.

Any Raney Nickel catalyst commonly used in the art may be used to reduce the ketimine and form sertraline. Examples of suitable catalysts include, but are not limited to, Kalcet™ 8030, Kalcet™ 1961, Kalcet™ 3801, Kalcet™ 9031, or Kalcet™ 2921 (Monarch Catalyst Pvt. Ltd, Dombivli(E), Thane-421 203, India). Preferably, the catalyst is Kalcet™ 8030, Kalcet™ 1961, or Kalcet™ 3801. The more preferred catalyst is Kalcet™ 8030. Table 1 exemplifies the ratios of cis:trans sertraline isomers formed based on the type of Raney Nickel used.

TABLE 1

Raney Nickel catalyst diastereomeric purity (% of Cis and Trans)

| | | Diastereomeric purity, % by GC | |
|---|---|---|---|
| Example | Raney Nickel catalyst | cis isomer | trans isomer |
| 1 | Kalcet ™ 8030 | 91 | 8.34 |
| 2 | Kalcet ™ 1961 | 89.9 | 8.8 |
| 3 | Kalcet ™ 3801 | 87.2 | 11.8 |
| 4 | Kalcet ™ 9031 | 86.5 | 12.2 |
| 5 | Kalcet ™ 2921 | 89.5 | 9.9 |

The following table provides detailed information about the contents of these catalysts:

| | | Standard Specifications | | |
|---|---|---|---|---|
| S. No. | Catalyst Grade | pH | Nickel Content | NB Activity Test | Bulk Density |
| 1. | KALCET-3801 | 9-10.5 | 90-92% | Min 50-60 ($H_2$) ml/gm/min. | 0.7-0.85 gram/ml (cc) |
| 2. | KALCET-2921 | 9-10.5 | 86-88% | Min 55-65 ($H_2$) ml/gm/min. | 0.5-0.6 gram/ml (cc) |
| 3. | KALCET-1961 | 9-10.5 | 86-88% | Min 55-60 ($H_2$) ml/gm/min. | 0.5-0.6 gram/ml (cc) |
| 4. | KALCET-8030 | 9-10.5 | 86-88% | Min 40-45 ($H_2$) ml/gm/min. | 0.70-0.78 gram/ml (cc) |
| 5. | KALCET-9031 | 9-10.5 | 88-90% | Min 55-65 ($H_2$) ml/gm/min. | 0.70-0.78 gram/ml (cc) |

Hydrogenation of the ketimine is preferably performed at about 3 kg/cm² to about 9 kg/cm², more preferably at about 5 kg/cm² to about 6 kg/Cm² over pressure of hydrogen at a suitable temperature for a sufficient period. Preferably, hydrogenation is carried out for about 2 to about 12 hours, more preferably about 5 hours to about 10 hours, and most preferably about 6 to about 7 hours. The reaction may be performed at a temperature of about 10° C. to about 40° C., preferably about 25° C. to about 35° C., and most preferably about 28° C. to about 30° C. The catalyst may be removed by any suitable method such as filtration. The filter cake may be washed with additional organic solvent after filtration.

The hydrogenated product, which contains sertraline and its isomer(s), may then be converted to sertraline HCl, in various manners. For example, hydrochloric acid may be provided as aqueous HCl, HCl gas, or HCl in a suitable organic solvent. In one embodiment, aqueous HCl (33%) in an amount of about 1 mol to about 2 mol equivalents, more preferably about 1.5 mol, is added to sertraline. Alternatively, HCl gas is bubbled into a solution of sertraline, which may be in the solvent used during the reduction of ketimine, or another suitable solvent such as, for example, n-butanol.

Sertraline hydrochloride may also be crystallized into various polymorphic forms, such as those disclosed in U.S. Pat. Nos. 6,500,987, 6,495,721 and 6,452,054, all incorporated herein by reference. For example, Sertraline hydrochloride Form II is prepared by contacting sertraline in a suitable solvent with hydrogen chloride gas at a temperature of about 0° C. to about 60° C., more preferably at about 30° C. to about 50° C., even more preferably at about 30° C. to about 45° C., and most preferably at about 40° C. to about 45° C. Salts such as sertraline mandelate may also be used as a starting material. Sertraline may be present in a solution or a slurry. Since sertraline is highly soluble in solvents such as n-butanol, a solution is preferred. Examples of suitable solvents are disclosed in U.S. Pat. Nos. 6,495,721 and 6,500,987.

Preferably, the desirable cis sertraline hydrochloride isomer is separated from the undesirable trans isomer. In one embodiment, the separation is carried out after conversion to the HCl salt. Optical resolution of the (±)-cis/trans-sertraline hydrochloride may be carried out in an appropriate organic solvent, such as ethanol, isopropanol, methanol, n-butanol, or iso-butanol. Ethanol is preferred.

In another embodiment, the separation is carried out before conversion to the HCl salt. This scheme entirely eliminates an intermediate in the scheme, namely the HCl salt of the trans isomer. Since resolution is carried out with sertraline as opposed to a sertraline HCl salt, non-polar solvents are preferred, particularly $C_6$ to $C_{12}$ aromatic and saturated hydrocarbons, such as toluene, xylene, benzene and cycohexane.

Regardless of the order, the resulting crude (+)-cis-sertraline mandelate is recrystallized in one embodiment to increase the purity of the product. Appropriate organic solvent include ethanol, isopropanol, methanol, n-butanol, or iso-butanol. Ethanol is preferred. Other optically active salts may also be used for resolution, such as, those obtained by reaction with tartaric acid, camphor sulphonic acid and lactic acid.

To obtain the HCl salt, the recrystallized (+)-cis-sertraline-mandelate is dissolved in organic solvent and the mandelic acid is removed with base, such as by washing the organic solution with an aqueous basic solution, e.g., 10-20% sodium hydroxide (NaOH) solution, or 10-20% potassium (KOH) solution. Generally, bases such as potassium hydroxide, sodium hydroxide, sodium carbonate ($Na_2CO_3$) and sodium bicarbonate ($NaHCO_3$) may be used. The (+)-cis-sertraline free base is isolated, dissolved in an appropriate organic solvent, and is treated with hydrochloric acid to give (+)-cis-sertraline hydrochloride. Details of HCl salt preparation are provided above.

The present invention provides a synthetic scheme suitable for preparation of sertraline hydrochloride without synthesis of isomeric mixture of N-Methyl-4-(3,4-Dichlorophenyl),1,2,34-tetrahydro-1-naphthalenamine hydrochloride (Key intermediate). The following preferred embodiment illustrates this scheme:

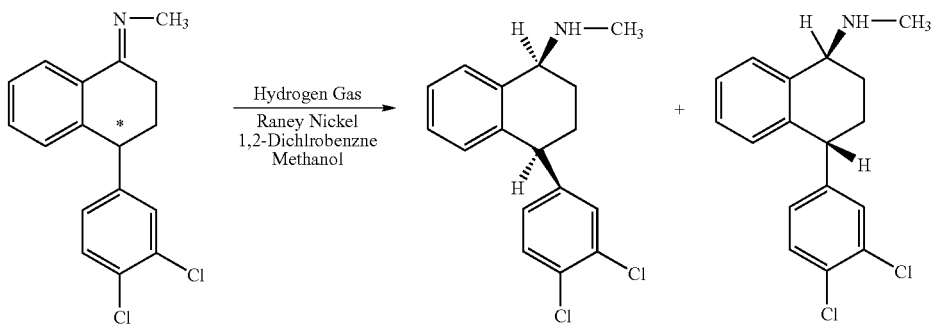
INTERMEDIATE-I
M.W. = 304.2
SERTRALINE
M.W. = 306
(Cis-Isomer)
SERTRALINE
M.W. = 306
(Trans-Isomer)
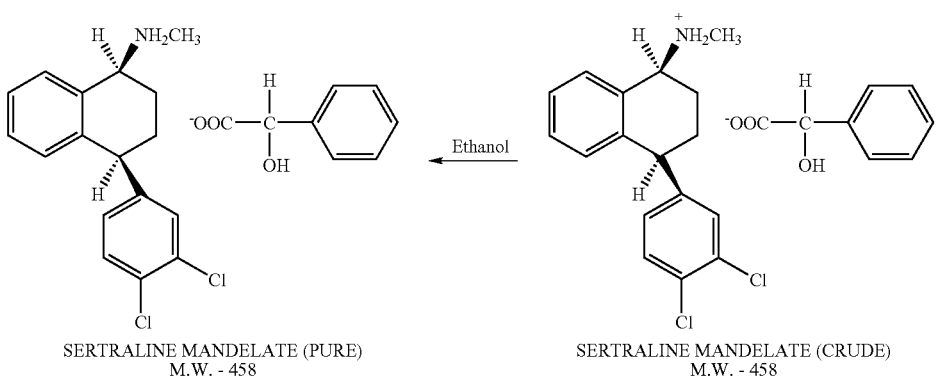
SERTRALINE MANDELATE (PURE)
M.W. - 458
SERTRALINE MANDELATE (CRUDE)
M.W. - 458
i. Sodium Hydroxide/Potassium Hydroxide
ii. Organic solvent
iii. HCl
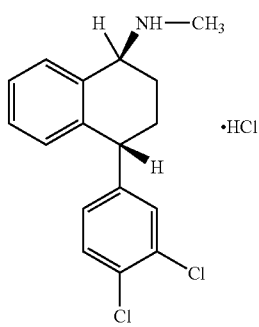
SERTRALINE HCl
M.W. = 342.5

To resolve the product of the hydrogenation, sertraline mother liquor is distilled to obtain a residue. Toluene and D(−)Mandelic acid are then combined with the residue. The resulting crude mandelate salt is recrystallized in ethanol to get pure of sertraline mandelate. The recrystallized (+)-cis-sertraline-mandelate can then be liberated and converted to the HCl salt as described above. This reaction scheme produces a product of high quality in high yields:

TABLE 1

| Steps | | U.S. Pat. No. 6809221 (w/w) | This Process (w/w) |
|---|---|---|---|
| Schiff's Base | | 1.01 | 0.95 |
| Sertraline Base | | — | — |
| Sertraline Mandelate | | 0.53 | 0.60 |
| Sertraline Mandelate (Pure) | | 0.79 | 0.85 |
| Overall yield | | 0.42 | 0.48 |
| Purity | Limits | | |
| Product Cis (1S,4S) | NLT-98.0% | 99.7-99.9% | 99.64% |
| Cis (1R,4R) | NMT-0.3% | ≈0.07% | Nil |
| Trans Isomer | NMT-0.3% | 0.20% | 0.185% |
| DCS-1 | NMT-0.2% | Complies | Complies |
| DCS-2 | NMT-0.2% | Complies | Complies |

The ketimine used in the process of the present invention may be prepared from sertralone. Sertralone may be condensed with methyl amine in the presence of an acid catalyst. Any suitable acid catalyst known in the art may be used, such as, for example, $TiCl_4$. See, e.g., U.S. Pat. No. 4,536,518.

The invention further encompasses a process of removing titanium from the ketamine formed from condensing sertralone with methyl amine in the presence of $TiCl_4$. The process of removing titanium comprises the steps of a) reacting sertralone with methylamine in a $C_6$ to $C_{12}$ hydrocarbon in the presence of $TiCl_4$ to obtain ketamine b) adding an additional amount of toluene to the reaction mixture, c) filtering the mixture to obtain an organic layer, d) washing the organic layer, e) treating the organic layer with activated carbon followed by filtration, f) removing the toluene by distillation to obtain a residue, g) combining the residue with cyclohexane; h) recovering the ketamine.

The organic solvent in the reaction mixture is preferably a $C_6$-$C_{12}$ aromatic hydrocarbon. More preferably, the organic solvent is toluene. The reaction is preferably heated to a temperature of about 45° C. to about 60° C. and stirred for about 20 minutes to about one hour.

Preferably, the reaction mixture is filtered through a filter such as a Celite or hyflo filter to obtain a cake, and the cake is then washed with an aqueous solvent, preferably water.

The organic layer is then treated with activated carbon. Preferably, the organic layer is heated to about 40° C. to 55° C. and then treated with 5% activated carbon for at least about 30 minutes. The activated carbon can be removed by filtration, such as by filtration through a Celite or hyflo filter. After the removal of activated carbon by filtration, the resulting cake may optionally be washed again with organic solvent, such as toluene.

Ketimine can be isolated by removing the organic solvent, such as by distillation under vacuum. A $C_6$ to $C_{12}$ saturated hydrocarbon, such as cyclohexane or n-hexane is added to the residue to aid recovery of the product. The solid is then be filtered and dried, such as under a vacuum (generally pressure below 100 mmHg).

In one embodiment, the present invention provides for sertraline of its HCl salt having a cis/trans ratio of about 9:1. In another embodiment, the present invention provides for sertraline of its HCl salt having less than about 0.1% of dechlorinated impurities as measured by HPLC or GC. Such product may be produced by carrying out the processes of the present invention.

Pharmaceutical compositions containing sertraline, or pharmaceutically-acceptable salts thereof, having less than about 0.1% of dechlorinated impurities and/or a cis/trans ratio of greater than about 9:1, and at least one pharmaceutically-acceptable excipient are also encompassed by the present invention.

Pharmaceutically-acceptable excipients are added to the pharmaceutical composition for a variety of purposes. For example, diluents increase the bulk of a solid pharmaceutical composition, and may make a pharmaceutical dosage form containing the composition easier for the patient and care giver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants may be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which may cause the product to have pitting and other surface irregularities. A lubricant may be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition include maltol, vanillin, ethyl vanillin, menthol, citric acid, fumaric acid, ethyl maltol and tartaric acid.

Solid and liquid compositions may also be dyed using any pharmaceutically acceptable colorant to improve their appearance and/or facilitate patient identification of the product and unit dosage level.

In liquid pharmaceutical compositions, sertraline hydrochloride and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

A liquid composition may also contain a buffer such as guconic acid, lactic acid, citric acid or acetic acid, sodium guconate, sodium lactate, sodium citrate or sodium acetate.

Selection of excipients and the amounts used may be readily determined by the formulation scientist based upon experience and consideration of standard procedures and reference works in the field.

The solid compositions include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges, as well as liquid syrups, suspensions and elixirs.

The dosage form may be a capsule containing the composition, preferably a powdered or granulated solid composition, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling may comprise any of the aforementioned blends and granulates that were described with reference to tableting, however, they are not subjected to a final tableting step.

Preferably, the pharmaceutical formulations are solid dosage forms in the form of a tablet for the oral administration of sertraline hydrochloride. The sertraline hydrochloride used for preparing a tablet may be in the form of fine crystals. Preferably, the fine crystals have a particle size distribution such that 100% of the particles are below 200 microns, more preferably below 100 microns and most preferably below about 50 microns.

The pharmaceutical composition may be used to inhibit serotonin reuptake in a mammal by administration to a mammal in need thereof.

Although certain presently preferred embodiments of the invention have been described herein, it will be apparent to those skilled in the art to which the invention pertains that variations and modifications of the described embodiments may be made without departing from the spirit and scope of the invention. Accordingly, it is intended that the invention be limited only to the extent required by the appended embodiments and the applicable rules of law.

1. Chromatographic Purity (by GC)

| | |
|---|---|
| Column: | DB-17 (30 m × 0.53 mm × 1.0 μm) |
| | J & W P/N 125-1732 or equivalent column |
| Detector | FID |
| Initial oven temperature | 215° C. |
| Initial time | 26 min. |
| Initial rate | 5° C./min. |
| Final oven temperature | 250° C. |
| Final time | 7 min. |
| Injector temperature | 160° C. |
| Detector temperature | 300° C. |

-continued

| | |
|---|---|
| Flow (helium) | 14.8 ml/min |
| Injection volume | 1 μL |
| Diluent | Hexane |

Temperature and flow rate may be varied in order to achieve the required system suitability.

2.1 System Suitability Preparation:

Weigh about 5 mg each of Sertraline Hydrochloride Racemate and 2,3-Iso-Sertraline standard into 25 ml test tube add 4 ml of 2.5% ammonium hydroxide solution followed by exactly 10 ml of n-Hexane. Shake well wait for phase separation and inject the organic (upper) layer.

2.2 Sample Preparation:

Weigh about 20 mg Sertraline Hydrochloride sample into a 25 ml test tube. Add 5 ml of 2.5% ammonium hydroxide solution followed by exactly 10 ml of n-hexane. Shake well wait for phase separation and inject the organic (upper) layer.

2.3 System Suitability Criteria

The resolution factor between the Sertraline peak and trans-Sertraline of not less than 1.7 should be achieved.

Typical retention times are 16.3 minutes for Sertraline and 17.4 minutes for trans-Sertraline.

2.4 Procedure

Inject equal amount of blank (Hexane) and sample in the chromatograph, continuing the chromatogram upto the end of the temperature gradient. Determine the areas for all peaks in each solution using a suitable integrator. Ignore the peaks due to blank. The relative retention times of the impurities are as follows:

| Name | RRT |
|---|---|
| DCS-3 | 0.29 |
| DCS-1 | 0.51 |
| DCS-2 | 0.54 |
| 2,3-Iso SRT | 0.92 |
| Sertraline | 1.00 |
| Trans-Sertraline | 1.07 |
| Sertralone | 1.27 |
| Schiffs Base | 1.55 |

EXAMPLES

Example 1

N-[4-(3,4-dichlorophenyl)-3,4-dihydro-1-(2H)naphthalenylidene]methanamine 100 g of Sertralone and 400 ml Toluene are charged into a reaction vessel fitted with a stirrer and gas inlet. The stirrer is started and the suspension is cooled to −15 to −10° C. A monomethylamine solution (72.4 g in 300 ml Toluene, 6.8 Mole) cooled to about −15 to −10° C. is combined with the sertralone suspension. Titanium Tetrachloride (17 ml, 0.45 mole) is added while the temperature is maintained at about −15 to −10° C. The temperature is slowly raised to about 55° C. to 60° C. and the mixture is stirred for about one hour. The product is more than 98% (GC Purity).

Toluene (200 ml) is added and the reaction is stirred for 20 minutes at about 55° C. to 60° C. The reaction mass is filtered through Celite and the cake is washed with 100 ml Toluene and filtered again. The toluene layer was washed with water (3×250 ml) and separated. The toluene layer was heated to about 40° C. to 55° C. and treated with 5% Charcoal for 30 minutes before being filtered through hyflo. The hyflo bed was washed with Toluene (25 ml) and then the toluene was distilled at about 45° C. to 55° C. under vacuum. After complete removal of toluene, cyclohexane (150 ml) was added. The solid was filtered and dried at 50° C. for 2 hours under vacuum. Kf=0.2.

Hydrogenation of the Schiff's Base (ketimine) obtained above by following the procedure in Example 3 gave a product of 93.77% Cis, 4.89% Trans, 1.05% Sertralone, 0.35% Schiff's Base. DCS-1 and DCS-2 are not detected.

Example 2

N-[4-(3,4-dichlorophenyl)-3,4-dihydro-1-(2H)naphthalenylidene]methanamine 100 gms of Sertralone and 400 ml Toluene are charged into a reaction vessel fitted with a strirrer and gas inlet. The stirrer is started and the suspension is cooled to about −15° C. to −10° C. A monomethylamine solution (72.4 g in 300 ml Toluene, 6.8 Mole) cooled to about −15° C. to −10° C. is combined with the suspension. Titanium Tetrachloride (17 ml, 0.45 mole) is added while the temperature is maintained at about −15° C. to −10° C. The temperature is slowly raised to about 55° C. to 60° C. and the mixture is stirred for 1 hour. The product is more than 98% (GC Purity).

Toluene (200 ml) is added and the reaction is stirred for 20 minutes at about 55° C. to 60° C. The reaction mass is filtered through Celite and the cake is washed with 100 ml toluene. The toluene layer was washed with water (3×250 ml) and separated. The toluene was distilled at 45° C. to 55° C. under vacuum. After complete removal of toluene, cyclohexane (150 ml) was added. The product was filtered and dried at 50° C. for 2 hours under vacuum. Kf=0.2.

Hydrogenation of the Schiff s Base (ketimine) obtained above by following the procedure in Example 3 gave a product of 94.66% Cis, 3.82% Trans, 0.62% Sertralone, 0.38% Schiff's Base. DCS-1 and DCS-2 are not detected Example 3

(1s-cis)-4-(3,4-dichlorophenyl)-1,2,3,4-tetrahydro-N-methyl-1-naphathalenamine hydrochloride (in methanol, o-dichlorobenzene as Dehalogenation Inhibitor)

N-[4-(3,4-dichlorophenyl)-3,4-dihydro-1(2H)naphthalenylidene]methanamine (Ketimine) (50 g), methanol (300 ml), Raney Nickel (0.15 g wet basis) and o-dichlorobenzene (50 ml) are charged into a reaction vessel. The mixture is hydrogenated at 5 to 6 kg/cm$^2$ over pressure of hydrogen for 6 to 7 hrs at about 28° C. to 30° C. The catalyst is removed by filtration and the cake is washed with 50 ml methanol. The cis to trans ratio is 87 to 89/9 to 13. The amount of dehalogenated by product is <0.1%. Sertraline racemate free base thus formed is treated with hydrochloric acid (24 ml, 33%) and predominantly isomer of sertraline HCl racemate is filtered [Cis>98%, trans<2%, dehalogenation product<0.1%, yield 0.86 to 0.88%].

Example-4

(1s-cis)-4-(3,4-dichlorophenyl)-1,2,3,4-tetrahydro-N-methyl-1-naphathalenamine hydrochloride (in methanol, chlorobenzene as Dehalogenation Inhibitor)

N-[4-(3,4-dichlorophenyl)-3,4-dihydro-1(2H)naphthalenylidene]methanamine (Ketimine) (50 g), methanol (300 ml), Raney Nickel (0.15 g wet basis) and chlorobenzene (25 ml) are charged into a reaction vessel. The mixture is hydrogenated at 5 to 6 kg/cm$^2$ over pressure of hydrogen for 6 to 7 hrs at about 28 to 30° C. The catalyst is removed by filtration and the cake is washed with 50 ml methanol. The cis to trans ratio is 87-89/9-13. The amount of dehalogenated by product is <0.1%. Sertraline racemate free base thus formed is treated with hydrochloric acid (24 ml, 33%) and predominantly isomer of sertraline HCl racemate is filtered [Cis>98%, trans<2%, dehalogenation product<0.1%, yield 0.86 to 0.88%].

Example-5

(1 s-cis)-4-(3,4-dichlorophenyl)-1,2,3,4-tetrahydro-N-methyl-1-naphathalenamine hydrochloride (in toluene, o-dichlorobenzene as Dehalogenation Inhibitor)

N-[4-(3,4-dichlorophenyl)-3,4-dihydro-1(2H)naphthalenylidene]methanamine (Ketimine) (50 g), toluene (300 ml), Raney Nickel (0.15 g wet basis) and o-dichlorobenzene (25 ml) are charged into a reaction vessel. The mixture is hydrogenated at 5 to 6 kg/cm$^2$ over pressure of hydrogen for 6 to 7 hrs at about 28 to 30° C. The catalyst is removed by filtration and the cake is washed with 50 ml methanol. The cis to trans ratio is 75 to 80/25 to 20. The amount of dehalogenated by product is <0.1%. Sertraline racemate free base thus formed is treated with hydrochloric acid (24 ml, 33%) and predominantly isomer of sertraline HCl racemate is filtered [Cis>95%, trans<5%, dehalogenation product<0.1%, yield 0.80 to 0.82%].

Example-6

(1 s-cis)-4-(3,4-dichlorophenyl)-1,2,3,4-tetrahydro-N-methyl-1-naphathalenamine hydrochloride (in tetrahydrofuran, o-dichlorobenzene as Dehalogenation Inhibitor)

N-[4-(3,4-dichlorophenyl)-3,4-dihydro-1(2H)naphthalenylidene]methanamine (Ketimine) (50 g), tetrahydrofuran (300 ml), Raney Nickel (0.15 g wet basis) and o-dichlorobenzene (25 ml) are charged into a reaction vessel. The mixture is hydrogenated at 5 to 6 kg/cm$^2$ over pressure of hydrogen for 6 to 7 hrs at about 28 to 30° C. The catalyst is removed by filtration and the cake is washed with 50 ml tetrahydrofuran. The cis to trans ratio is 85 to 87/15 to 13. The amount of dehalogenated byproduct is <0.1%. Sertraline racemate free base thus formed is treated with hydrochloric acid (24 ml, 33%) and predominantly isomer of sertraline HCl racemate is filtered [Cis>95%, trans<5%, dehalogenation product<0.1%, yield 0.75 to 0.78%].

Example-7

(1s-cis)-4-(3,4-dichlorophenyl)-1,2,3,4-tetrahydro-N-methyl-1-naphathalenamine hydrochloride (in Ethyl Acetate, o-dichlorobenzene as Dehalogenation Inhibitor)

N-[4-(3,4-dichlorophenyl)-3,4-dihydro-1(2H)naphthalenylidene]methanamine (Ketimine) (50 g), Ethyl acetate(300 ml), Raney Nickel (0.15 g wet basis) and o-dichlorobenzene (25 ml) are charged into a reaction vessel. The mixture is hydrogenated at 5 to 6 kg/cm$^2$ over pressure of hydrogen for 6 to 7 hrs at about 28 to 30° C. The catalyst is removed by filtration and the cake is washed with 50 ml ethyl acetate. The amount of dehalogenated by product is <0.1%. Sertraline racemate free base thus formed is treated with hydrochloric acid (24 ml, 33%) and predominantly isomer of sertraline HCl racemate is filtered [Cis>98%, trans<2%, dehalogenation product<0.1%, yield 0.78 to 0.80%].

Example-8

(1s-cis)-4-(3,4-dichlorophenyl)-1,2,3,4-tetrahydro-N-methyl-1-naphathalenamine hydrochloride (in dimethylformamide, o-dichlorobenzene as Dehalogenation Inhibitor)

N-[4-(3,4-dichlorophenyl)-3,4-dihydro-1(2H)naphthalenylidene]methanamine (Ketimine) (50 g), dimethylformamide (300 ml), Raney Nickel (0.15 g wet basis) and o-dichlorobenzene (25 ml) are charged into a reaction vessel. The mixture is hydrogenated at 5 to 6 kg/cm$^2$ over pressure of hydrogen for 12 to 13 hrs at about 28 to 30° C. The catalyst is removed by filtration and the cake is washed with 50 ml methanol. The amount of dehalogenated by product is <0.1%. Sertraline racemate free base thus formed is treated with hydrochloric acid (24 ml, 33%) and predominantly isomer of sertraline HCl racemate is filtered [Cis>95%, trans<5%, dehalogenation product<0.1%, yield 0.72 to 0.75%].

Example-9

(1s-cis)-4-(3,4-dichlorophenyl)-1,2,3,4-tetrahydro-N-methyl-1-naphathalenamine hydrochloride (in ethanol, o-dichlorobenzene as Dehalogenation Inhibitor)

N-[4-(3,4-dichlorophenyl)-3,4-dihydro-1(2H)naphthalenylidene]methanamine (Ketimine) (50 g), ethanol (300 ml), Raney Nickel (0.15 g wet basis) and o-dichlorobenzene (50 ml) are charged into a reaction vessel. The mixture is hydrogenated at 5 to 6 kg/cm$^2$ over pressure of hydrogen for 6 to 7 hrs at about 28 to 30° C. The catalyst is removed by filtration and the cake is washed with 50 ml ethanol. The cis to trans ratio is 82 to 85/18 to 15. The amount of dehalogenated by product is <0.1%. Sertraline racemate free base thus formed is treated with hydrochloric acid (24 ml, 33%) and predominantly isomer of sertraline HCl racemate is filtered [Cis>98%, trans<2%, dehalogenation product<0.1%, yield 0.80 to 0.82%].

Example-10

(1s-cis)-4-(3,4-dichlorophenyl)-1,2,3,4-tetrahydro-N-methyl-1-naphathalenamine hydrochloride (in isopropyl alcohol, o-dichlorobenzene as Dehalogenation Inhibitor)

N-[4-(3,4-dichlorophenyl)-3,4-dihydro-1(2H)naphthalenylidene]methanamine (Ketimine) (50 g), IPA (300 ml), Raney Nickel (0.15 g wet basis) and o-dichlorobenzene (50 ml) are charged into a reaction vessel. The mixture is hydrogenated at 5 to 6 kg/cm$^2$ over pressure of hydrogen for 6 to 7 hrs at about 28 to 30° C. The catalyst is removed by filtration and the cake is washed with 50 ml IPA. The amount of dehalogenated by product is <0.1%. Sertraline racemate free base thus formed is treated with hydrochloric acid (24 ml, 33%) and predominantly isomer of sertraline HCl racemate is filtered [Cis>95%, trans<5%, dehalogenation product<0.1%, yield 0.80 to 0.82%].

Example-11

(1s-cis)-4-(3,4-dichlorophenyl)-1,2,3,4-tetrahydro-N-methyl-1-naphathalenamine hydrochloride (in methanol, DCM as Dehalogenation Inhibitor)

N-[4-(3,4-dichlorophenyl)-3,4-dihydro-1(2H)naphthalenylidene]methanamine (Ketimine) (50 g), methanol (300 ml), Raney Nickel (0.15 g wet basis) and DCM (12.5 ml) are charged into a reaction vessel. The mixture is hydrogenated at 5 to 6 kg/cm$^2$ over pressure of hydrogen for 6 to 7 hrs at about 28 to 30° C. The catalyst is removed by filtration and the cake is washed with 50 ml methanol. The amount of dehalogenated by product is <0.1%. Sertraline racemate free base thus formed is treated with hydrochloric acid (24 ml, 33%) and predominantly isomer of sertraline HCl racemate is filtered [Cis>95%, trans<5%, dehalogenation product<0.1%, yield 0.76%].

Example-12

(1s-cis)-4-(3,4-dichlorophenyl)-1,2,3,4-tetrahydro-N-methyl-1-naphathalenamine hydrochloride (in methanol, o-chlorotoluene as Dehalogenation Inhibitor).

N-[4-(3,4-dichlorophenyl)-3,4-dihydro-1(2H)naphthalenylidene]methanamine (Ketimine) (50 g), methanol (300 ml), Raney Nickel (0.15 g wet basis) and o-chlorotoluene (50 ml) are charged into a reaction vessel. The mixture is hydrogenated at 5 to 6 kg/cm$^2$ over pressure of hydrogen for 6 to 7 hrs at about 28 to 30° C. The catalyst is removed by filtration and the cake is washed with 50 ml methanol. The amount of dehalogenated by product is <0.1%. Sertraline racemate free base thus formed is treated with hydrochloric acid (24 ml, 33%) and predominantly isomer of sertraline HCl racemate is filtered [Cis>95%, trans<5%, dehalogenation product<0.1%, yield 0.76%].

Example 13

Salt Formation in 18% Reducing Quantity of Methanol (1s-cis)-4-(3,4-dichlorophenyl)-1,2,3,4-tetrahydro-N-methyl-1-nahathalenamine hydrochloride (in methanol, o-dichlorobenzene as Dehalogenation Inhibitor)

N-[4-(3,4-dichlorophenyl)-3,4-dihydro-1(2H)naphthalenylidene]methanamine (Ketimine) (50 g), methanol (300 ml), Raney Nickel (0.15 g wet basis) and o-dichlorobenzene (50 ml) are charged into a reaction vessel. The mixture is hydrogenated at 5 to 6 kg/cm$^2$ over pressure of hydrogen for 6 to 7 hrs at about 28° C. to 30° C. The catalyst is removed by filtration and the cake is washed with 50 ml methanol. After distillation of 18% Methanol, sertraline racemate free base thus formed is treated with hydrochloric acid (24 ml, 33%) and predominantly isomer of sertraline HCl racemate is filtered [Cis 97.25%, trans 2.30%, Sertralone 0.05%, Schiff's base not detected, dehalogenation product (DCS-1 0.07% DCS-2 0.09%), yield 0.93 w/w].

Example 14

Salt Formation in 20% Reducing Quantity of Methanol (1s-cis)-4-(3,4-dichlorophenyl)-1,2,3,4-tetrahydro-N-methyl-1-naphathalenamine hydrochloride (in methanol, o-dichlorobenzene as Dehalogenation Inhibitor)

N-[4-(3,4-dichlorophenyl)-3,4-dihydro-1(2H)naphthalenylidene]methanamine (Ketimine) (50 g), methanol (300 ml), Raney Nickel (0.15 g wet basis) and o-dichlorobenzene (50 ml) are charged into a reaction vessel. The mixture is hydrogenated at 5 to 6 kg/cm$^2$ over pressure of hydrogen for 6 to 7 hrs at about 28° C. to 30° C. The catalyst is removed by filtration and the cake is washed with 50 ml methanol. After distillation of 20% methanol, sertraline racemate free base thus formed is treated with hydrochloric acid (24 ml, 33%) and predominantly isomer of sertraline HCl racemate is filtered [Cis 98.59%, trans 1.57%, Sertralone 0.03%, Schiff's base not detected, dehalogenation product (DCS-1 0.09% DCS-2 0.04%), yield 0.97 w/w].

Example 15

Salt Formation in 22% Reducing Quantity of Methanol (1s-cis)-4-(3,4-dichlorophenyl)-1,2,3,4-tetrahydro-N-methyl-1-naphathalenamine hydrochloride (in methanol, o-dichlorobenzene as Dehalogenation Inhibitor)

N-[4-(3,4-dichlorophenyl)-3,4-dihydro-1(2H)naphthalenylidene]methanamine (Ketimine) (50 g), methanol (300 ml), Raney Nickel (0.15 g wet basis) and o-dichlorobenzene (50 ml) are charged into a reaction vessel. The mixture is hydrogenated at 5 to 6 kg/cm$^2$ over pressure of hydrogen for 6 to 7 hrs at about 28° C. to 30° C. The catalyst is removed by filtration and the cake is washed with 50 ml methanol. After distillation of 22% Methanol, sertraline racemate free base thus formed is treated with hydrochloric acid (24 ml, 33%) and predominantly isomer of sertraline HCl racemate is filtered [Cis 97.77%, trans 1.41%, sertralone 0.06%, Schiff's base not detected, dehalogenation product (DCS-1 0.08% DCS-2 0.05%), yield 1.01 w/w].

Example 16

Salt Formation in 40% Reducing Quantity of Methanol (1s-cis)-4-(3,4-dichlorophenyl)-1,2,3,4-tetrahydro-N-methyl-1-naphathalenamine hydrochloride (in methanol, o-dichlorobenzene as Dehalogenation Inhibitor)

N-[4-(3,4-dichlorophenyl)-3,4-dihydro-1(2H)naphthalenylidene]methanamine (Ketimine) (50 g), methanol (300 ml), Raney Nickel (0.15 g wet basis) and o-dichlorobenzene (50 ml) are charged into a reaction vessel. The mixture is hydrogenated at 5 to 6 kg/cm$^2$ over pressure of hydrogen for 6 to 7 hrs at about 28° C. to 30° C. The catalyst is removed by filtration and the cake is washed with 50 ml methanol. After distillation of 40% methanol, sertraline racemate free base thus formed is treated with hydrochloric acid (24 ml, 33%) and predominantly isomer of sertraline HCl racemate is filtered [Cis 97.96%, trans 1.89%, sertralone not detected, Schiff's base not detected, dehalogenation product (DCS-1 0.01%, DCS-2 0.03%), yield 0.95 w/w].

Example-17

Optical Resolution of Sertraline Hydrochloride (±)-Sertraline hydrochloride (5 g) was dissolved in ethanol (20 mL) and KOH powder (85%) was added to the solution. The slurry was stirred at room temperature for 2.5 hrs. After stirring the solids were removed by filtration and the solution was treated with D-(−)-mandelic acid (2.66 g). Precipitation occurred and the stirring was continued for 24 hours. (+)-Sertraline-mandelate was isolated by filtration and washed with ethanol and then dried to yield 2.70 g of (+)-sertraline-mandelate.

Example-18

Preparation of Sertraline Hydrochloride Form II (Industrial Scale)

Sertraline base (27 kg) was dissolved in 105 kg of n-butanol. The solution was treated for 1 hour with 1 kg carbon at 40 to 45° C. and filtered and washed with 25 kg n-butanol. The solution was reheated to 40-45° C. and the achieved temperature was kept constant during the gas flow and filtration. Hydrogen chloride gas was added at the rate of 4.5-5 kg/hr for the duration of 1 hour until pH 0.5 or less was reached. Immediately thereafter, the slurry was filtered at 40-45° C. The cake was washed with 25 kg of n-butanol, and dried for about 4 hours at 80° C. The yield was 70% (21.2 kg).

Example 19(a)

Preparation of (1s-cis)-4-(3,4-dichlorophenyl)-1,2,3,4-tetrahydro-N-methyl-1-naphathalenamine hydrochloride (in methanol, o-dichlorobenzene as Dehalogenation Inhibitor)

N-[4-(3,4-dichlorophenyl)-3,4-dihydro-1(2H)naphthalenylidene]methanamine (Ketimine) (50 g), methanol (300 ml), Raney Nickel (0.15 g wet basis) and o-dichlorobenzene (50 ml) are charged into a reaction vessel. The mixture is hydrogenated at 5 to 6 kg/cm$^2$ over pressure of hydrogen for 6 to 7 hrs at about 28° C. to 30° C. The catalyst is removed by filtration and the cake is washed with 50 ml methanol. The cis to trans ratio is 87 to 89/9 to 13. The amount of dehalogenated by product is <0.1%.

Example 19(b)

Preparation of (1S,4S)-N-methyl-4-(3,4-dichlorophenyl)-1,2,3,4-tetrahydro-1-methyl-1-naphathalenamine Mandelate Sertraline Racemate free base thus formed is distilled out to get residue and added fresh Toluene. This solution then heated to 75-80° C. and added D(−)Mandelic Acid. Heated to reaction mass to 75-80° C. for 30 to 45 Minutes and finally cooled to 14-25° C. The obtained crude Mandelate salt having SS Sertraline Mandelate>95% RR isomer<2%, SR/RS isomer<2.5%, yield 0.6 w/w.

The obtained curde Mandelate dissolved in 25 to 28 volume hot absolute ethanol and heated for 30 to 40 Minute at 78° C. (±2° C.). After cooling on crystallization it gives pure Sertraline Mandelate Cis(1S,4S)-N-methyl-4-(3,4-dichlorophynyl),1,2,3,4-tetrahyro-1-naphthalenamine Mandelate>99%, RR isomer<0.2%, RS/SR isomer<0.2%.

Example 19(c)

Preparation of Cis (1S,4S)-N-methyl-4-(3,4-dichlorophenyl)-1,2,3,4-tetrahydro-1-naphathalenamine hydrochloride The recrystallized (+)-cis-sertraline-precipitant, e.g., (+)-cis-sertraline-mandelate, is dissolved in organic solvent and the mandelic acid is removed with base, such as, by washing the organic solution with aqueous basic solutions, e.g., 10-20% sodium hydroxide (NaOH) solution, or 10-20% potassium (KOH) solution. The (+)-cis-sertraline free base is isolated, dissolved in an appropriate organic solvent, and is treated with hydrochloric acid. (+)-Cis-Sertraline hydrochloride is precipitated and dried to give (+)-cis-sertraline hydrochloride.

What is claimed is:

1. A process of preparing sertraline comprising the step of reducing ketimine with Raney Nickel under a hydrogen atmosphere, wherein the ketamine is in a mixture with at least one halogenated hydrocarbon and at least one organic solvent.

2. The process of claim 1, wherein the halogenated hydrocarbon is a $C_1$-$C_7$ hydrocarbon or mixtures thereof.

3. The process of claim 1, wherein the halogenated hydrocarbon is a chlorinated aromatic hydrocarbon, chlorinated $C_1$-$C_4$ alkane or mixtures thereof.

4. The process of claim 1, wherein the halogenated hydrocarbon is selected from the group consisting of chlorobenzene, o- or p-dichlorobenzene, dichloromethane, and chlorotoluene.

5. The process of claim 1, wherein the halogenated hydrocarbon is present in an amount of about 0.01 mol to about 3.0 mol equivalent of the ketimine.

6. The process of claim 5, wherein the halogenated hydrocarbon is present in an amount of about 1.0 mol equivalent of the ketimine.

7. The process of claim 1, wherein the organic solvent is at least one of a $C_1$-$C_4$ alcohol, $C_3$-$C_6$ ester, $C_6$-$C_{12}$ aromatic hydrocarbon, $C_2$-$C_8$ ether, $C_3$-$C_7$ amide or mixtures thereof.

8. The process of claim 7, wherein the organic solvent is selected from the group consisting of methanol, ethanol, isopropanol, toluene, tetrahydrofuran, ethyl acetate, dimethylformamide and mixtures thereof.

9. The process of claim 8, wherein the organic solvent is methanol.

10. The process of claim 1, wherein the reduction is carried out under a hydrogen atmosphere of about 3 kg to about 9 kg.

11. The process of claim 1, wherein the reduction is carried out at a temperature of about 10° C. to about 40° C.

12. The process of claim 1, wherein the reduction is carried out for about 2 to about 12 hours.

13. The process of claim 1, wherein the ketamine used for the reduction is prepared by condensing sertralone with methyl amine in the presence of an acid catalyst in toluene.

14. The process of claim 1, further comprising converting sertraline of claim 1 to sertraline HCl.

15. The process of claim 1 or 14, wherein the reduced product has less than about 0.1% of dechlorinated impurities as measured by High Pressure Liquid Chromatography or Gas Chromatography.

16. The process of claim 14, further comprising a preliminary step of separating cis sertraline from the resulting mixture of cis and trans diastereoisomers.

17. The process of claim 16, wherein the separation is carried out by reacting cis sertraline present in the mixture with D(-)Mandelic without an intervening step of forming an HCl salt.

18. The process of claim 17, wherein the sertraline has a cis/trans ratio of greater than about 9:1.

19. The process of claim 1, wherein an acid catalyst is used in the reaction.

20. The process of claim 19, wherein the acid catalyst is $TiCl_4$.

21. The process of claim 20, further comprising removing titanium from the ketamine before reduction.

22. The process of claim 21, wherein the process of removing titanium from the ketimine comprises the steps of:
   a) adding an additional amount of toluene to the reaction mixture;
   b) filtering the mixture to obtain an organic layer;
   c) washing the organic layer;
   d) treating the organic layer with activated carbon followed by filtration;
   e) removing the toluene by distillation to obtain a residue;
   f) combining the residue with cyclohexane; and
   g) recovering the ketamine.

23. The process of claim 22, wherein the mixture of step a) is heated to a temperature of about 45° C. to about 60° C. and stirred for about 20 minutes to about one hour.

* * * * *